United States Patent
Russell et al.

(10) Patent No.: US 10,551,460 B1
(45) Date of Patent: Feb. 4, 2020

(54) METHOD OF GENERATING REPRODUCIBLE QUANTITATIVE MAGNETIC RESONANCE DATA

(71) Applicant: ARIZONA BOARD OF REGENTS ON BEHALF OF THE UNIVERSITY OF ARIZONA, Tucson, AZ (US)

(72) Inventors: Gregory Paul Russell, Cleveland, OH (US); Theodore P. Trouard, Tucson, AZ (US); Jean-Philippe Galons, Tucson, AZ (US); Eriko Yoshimaru, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1155 days.

(21) Appl. No.: 14/680,769

(22) Filed: Apr. 7, 2015

Related U.S. Application Data

(60) Provisional application No. 61/979,961, filed on Apr. 15, 2014, provisional application No. 61/976,713, filed on Apr. 8, 2014.

(51) Int. Cl.
*G01R 33/54* (2006.01)
*G01N 24/08* (2006.01)

(52) U.S. Cl.
CPC ......... *G01R 33/543* (2013.01); *G01N 24/087* (2013.01)

(58) Field of Classification Search
CPC .............. G01R 33/543; G01R 33/5608; G01R 33/5611; G01R 33/4835; G01R 33/4828; G01N 24/087
USPC ........................................................ 324/309
See application file for complete search history.

(56) References Cited

U.S. PATENT DOCUMENTS

| | | | | | |
|---|---|---|---|---|---|
| 4,706,024 | A | * | 11/1987 | Dumoulin | G01R 33/56 324/309 |
| 5,000,182 | A | * | 3/1991 | Hinks | A61B 5/0456 600/413 |
| 5,588,431 | A | * | 12/1996 | Mani | A61B 5/0263 324/307 |

(Continued)

OTHER PUBLICATIONS

Mani, Sanjay, et al. "Background suppression with multiple inversion recovery nulling: applications to projective angiography." Magnetic resonance in medicine 37.6 (1997): 898-905.*

(Continued)

*Primary Examiner* — Christopher P McAndrew
(74) *Attorney, Agent, or Firm* — Nguyen Tarbet

(57) ABSTRACT

The present invention discloses a method of obtaining reproducible quantitative magnetic resonance data about a sample to be analyzed, which allows for the rapid collection of a large amount of data that is well suited for quantitative analysis. In some embodiments, the method comprises performing a nulling sequence, where the nulling sequence comprises a series of applied changes to the magnetic field of the sample, which reduces all components of the magnetization in the sample to near zero or zero magnitude, within measurable limits; and performing at least one excitation step, where each excitation step comprises applying an excitation (radio frequency) pulse to the sample, followed by a measurement of magnetic resonance data.

3 Claims, 4 Drawing Sheets

(56) References Cited

U.S. PATENT DOCUMENTS

| | | | | |
|---|---|---|---|---|
| 6,307,368 | B1* | 10/2001 | Vasanawala | G01R 33/5613 324/300 |
| 2004/0113613 | A1* | 6/2004 | Markl | G01R 33/5613 324/306 |
| 2005/0030024 | A1* | 2/2005 | Golay | G01R 33/4828 324/307 |
| 2005/0215881 | A1* | 9/2005 | Van Zijl | G01R 33/483 600/410 |
| 2009/0315559 | A1* | 12/2009 | Herzka | G01R 33/5613 324/309 |
| 2014/0316251 | A1* | 10/2014 | Walker-Samuel | G01R 33/56316 600/419 |

OTHER PUBLICATIONS

Mani, Sanjay, et al. "Background suppression with multiple inversion recovery nulling: applications to projective angiography." Magnetic resonance in medicine 37.6 (1997): 898-905. (Year: 1997).*

Callaghan, P.T., Principles of Nuclear Magnetic Resonance Microscopy. London: Oxford University Press, 1993.

Moseley, M.E., et al., Early detection of regional cerebral ischemia in cats: Comparison of diffusion- and T2-weighted MRI and spectroscopy. Magnetic Resonance in Medicine, 1990. 14(2): p. 330-346.

Warach, S., et al., Acute human stroke studied by whole brain echo planar diffusion-weighted magnetic resonance imaging. Annals of Neurology, 1995. 37(2): p. 231-241. 4.

Tanner, J.E. and E.O. Stejskal, Restricted Self-Diffusion of Protons in Colloidal Systems by the Pulsed-Gradient, Spin-Echo Method. The Journal of Chemical Physics, 1968. 49(4): p. 1768-1777.

Neuman, C.H., Spin echo of spins diffusing in a bounded medium. The Journal of Chemical Physics, 1974. 60(11): p. 4508-4511.

De Swiet, T.M. and P.N. Sen, Decay of nuclear magnetization by bounded diffusion in a constant field gradient. Journal of Chemical Physics, 1994. 100(8): p. 5597.

Stanisz, G.J., et al., An analytical model of restricted diffusion in bovine optic nerve. Magnetic Resonance in Medicine, 1997. 37(1): p. 103-111.

Murday, J.S. and R.M. Cotts, Self-Diffusion Coefficient of Liquid Lithium. The Journal of Chemical Physics, 1968. 48 (11): p. 4938-4945.

Balinov, B., et al., The NMR Self-Diffusion Method Applied to Restricted Diffusion. Simulation of Echo Attenuation from Molecules in Spheres and between Planes. Journal of Magnetic Resonance, Series A, 1993. 104(1): p. 17-25.

Carr, H.Y. and E.M. Purcell, Effects of Diffusion on Free Precession in Nuclear Magnetic Resonance Experiments. Physical Review, 1954. 94(3): p. 8.

Torrey, H.C., Bloch Equations with Diffusion Terms. Physical Review, 1956. 104(3): p. 563-565.

Finkelstien, A., Water movement through lipid bilayers, pores, and plasma: Theory and reality. John Wiley & Sons, 1987.

Fieremans, E., et al., Monte Carlo study of a two-compartment exchange model of diffusion. NMR in Biomedicine, 2010. 23(7): p. 711-724.

Sukstanskii, A.L., D.A. Yablonskiy, and J.J.H. Ackerman, Effects of permeable boundaries on the diffusion-attenuated MR signal: insights from a one-dimensional model. Journal of Magnetic Resonance, 2004. 170(1): p. 56-66.

Vestergaard-Poulsen, P., et al., Microstructural changes in ischemic cortical gray matter predicted by a model of diffusion-weighted MRI. Journal of Magnetic Resonance Imaging, 2007. 26(3): p. 529-540.

Schoeniger, J.S., et al., Relaxation-Time and Diffusion NMR Microscopy of Single Neurons. Journal of Magnetic Resonance, Series B, 1994. 103(3): p. 261-273.

Buckley, D.L., et al., The effect of ouabain on water diffusion in the rat hippocampal slice measured by high resolution NMR imaging. Magnetic Resonance in Medicine, 1999. 41(1): p. 137-142.

Callaghan, P.T., A Simple Matrix Formalism for Spin Echo Analysis of Restricted Diffusion under Generalized Gradient Waveforms. Journal of Magnetic Resonance, 1997. 129(1): p. 74-84.

Sukstanskii, A.L. and D.A. Yablonskiy, Effects of Restricted Diffusion on MR Signal Formation. Journal of Magnetic Resonance, 2002. 157(1): p 92-105.

Harkins, K.D., et al., Assessment of the effects of cellular tissue properties on ADC measurements by numerical simulation of water diffusion. Magnetic Resonance in Medicine, 2009. 62(6): p. 1414-1422.

Szafer, A., et al., Diffusion-weighted imaging in tissues: Theoretical models. NMR in Biomedicine, 1995. 8(7): p. 289-296.

Harkins, K.D., et al., Changes in intracellular water diffusion and energetic metabolism in response to ischemia in perfused C6 rat glioma cell. Magnetic Resonance in Medicine, 2011. 66(3): p. 859-867.

Trouard, T.P., et al., Ischemia-induced changes of intracellular water diffusion in rat glioma cell cultures. Magnetic Resonance in Medicine, 2008. 60(2): p. 258-264.

Russell, G., et al., A finite difference method with periodic boundary conditions for simulations of diffusion-weighted magnetic resonance experiments in tissue. Physics in Medicine and Biology, 2012. 57(4): p. N35.

Assaf, Y. and Y. Cohen, Non-Mono-Exponential Attenuation of Water andN-Acetyl Aspartate Signals Due to Diffusion in Brain Tissue. Journal of Magnetic Resonance, 1998. 131(1): p. 69-85.

Mills, R., Self-diffusion in normal and heavy water in the range 1-45.deg. The Journal of Physical Chemistry, 1973. 77 (5): p. 685-688.

Sykova, E., et al., Extracellular Volume Fraction and Diffusion Characteristics During Progressive Ischemia and Terminal Anoxia in the Spinal Cord of the Rat. J Cereb Blood Flow Metab, 1994. 14(2): p. 301-311.

Silva, M.D., et al., Separating changes in the intra- and extracellular water apparent diffusion coefficient following focal cerebral ischemia in the rat brain. Magnetic Resonance in Medicine, 2002. 48(5): p. 826-837.

Pfeuffer, J., et al., Restricted diffusion and exchange of intracellular water: theoretical modelling and diffusion time dependence of 1H NMR measurements on perfused glial cells. NMR in Biomedicine, 1998. 11(1): p. 19-31.

Does, M.D. and J.C. Gore, Compartmental study of diffusion and relaxation measured in vivo in normal and ischemic rat brain and trigeminal nerve. Magnetic Resonance in Medicine, 2000.43(6): p. 837-844.

Duong, T.Q., et al., Evaluation of extra- and intracellular apparent diffusion in normal and globally ischemic rat brain via 19F NMR. Magnetic Resonance in Medicine, 1998. 40(1): p. 1-13.

Anderson, A.W., et al., Effects of cell volume fraction changes on apparent diffusion in human cells. Magnetic Resonance Imaging, 2000. 18(6): p. 689-695.

Does, M.D. and J.C. Gore, Compartmental study of T1 and T2 in rat brain and trigeminal nerve in vivo. Magnetic Resonance in Medicine, 2002.47(2): p. 274-283.

Katz, R., Biomarkers and Surrogate Markers: An FDA Perspective. NeuroRX, 2004. 1(2): p. 189-195.

Tofts, P.S. and E.P.G.H. Boulay, Towards quantitative measurements of relaxation times and other parameters in the brain. Neuroradiology, 1990. 32(5): p. 407-415.

Binks, D.A., et al., Quantitative parametric MRI of articular cartilage: a review of progress and open challenges. British Journal of Radiology, 2012. 86(1023).

Warntjes, J.B.M., O. Dahlqvist, and P. Lundberg, Novel method for rapid, simultaneous T1, T*2, and proton density quantification. Magnetic Resonance in Medicine, 2007. 57(3): p. 528-537.

Deoni, S.C.L., et al., Gleaning multicomponent T1 and T2 information from steady-state imaging data. Magnetic Resonance in Medicine, 2008. 60(6): p. 1372-1387.

(56) References Cited

OTHER PUBLICATIONS

Neeb, H., K. Zilles, and N.J. Shah, A new method for fast quantitative mapping of absolute water content in vivo. NeuroImage, 2006. 31(3): p. 1156-1168.
Ma, D., et al., Magnetic resonance fingerprinting. Nature, 2013. 495(7440): p. 187-192.
Deoni, S.C.L., B.K. Rutt, and T.M. Peters, Rapid combined T1 and T2 mapping using gradient recalled acquisition in the steady state. Magnetic Resonance in Medicine, 2003. 49(3): p. 515-526.
Deoni, S.C.L., T.M. Peters, and B.K. Rutt, High-resolution T1 and T2 mapping of the brain in a clinically acceptable time with DESPOT1 and DESPOT2. Magnetic Resonance in Medicine, 2005. 53(1): p. 237-241.
Freeman, R. and H.D.W. Hill, Phase and intensity anomalies in fourier transform NMR. Journal of Magnetic Resonance (1969), 1971. 4(3): p. 366-383.
Bieri, O. and K. Scheffler, Fundamentals of balanced steady state free precession MRI. Journal of Magnetic Resonance Imaging, 2013. 38(1): p. 2-11.
Bloch, F., Nuclear Induction. Physical Review, 1946. 70(7-8): p. 460-474.
Bloch, F., The Principle of Nuclear Induction. Science, 1953. 118(3068): p. 425-430.
McConnell, H.M., Reaction Rates by Nuclear Magnetic Resonance. The Journal of Chemical Physics, 1958. 28(3): p. 130-431.
Cao, Z., et al., Bloch-based MRI system simulator considering realistic electromagnetic fields for calculation of signal, noise, and specific absorption rate. Magnetic Resonance in Medicine, 2013.
Wansapura, J.P., et al., NMR relaxation times in the human brain at 3.0 tesla. Journal of Magnetic Resonance Imaging, 1999. 9(4): p. 531-538.
Ernst, R.R. and W.A. Anderson, Application of Fourier Transform Spectroscopy to Magnetic Resonance. Review of Scientific Instruments, 1966. 37(1): p. 93-102.
Freeman, R. and H.D.W. Hill, Fourier Transform Study of NMR Spin–Lattice Relaxation by "Progressive Saturation". The Journal of Chemical Physics, 1971. 54(8): p. 3367-3377.
Freeman, R. and H.D.W. Hill, High-Resolution Study of NMR Spin Echoes: "J Spectra". The Journal of Chemical Physics, 1971. 54(1): p. 301-313.
Lankford, C.L. and M.D. Does, On the inherent precision of mcDESPOT. Magnetic Resonance in Medicine, 2012. 69 (1): p. 127-136.
Aliu, S. O., Wilmes, L. J., Moasser, M. M., Hann, B. C., Li, K. L., Wang, D. & Hylton, N. M. (2009) MRI methods for evaluating the effects of tyrosine kinase inhibitor administration used to enhance chemotherapy efficiency in a breast tumor xenograft model. J Magn Reson Imaging, 29, 1071-9.
Callaghan, P. T. (1997) A simple matrix formalism for spin echo analysis of restricted diffusion under generalized gradient waveforms. J Magn Reson, 129, 74-84.
Chenevert, T. L., Stegman, L. D., Taylor, J. M., Robertson, P. L., Greenberg, H. S., Rehemtulla, A. & Ross, B. D. (2000) Diffusion magnetic resonance imaging: an early sun-ogate marker of therapeutic efficacy in brain tumors. J Natl Cancer Inst, 92, 2029-36.
Cui, Y., Zhang, X. P., Sun, Y. S., Tang, L. & Shen, L. (2008) Apparent diffusion coefficient: potential imaging biomarker for prediction and early detection of response to chemotherapy in hepatic metastases. Radiology, 248, 894-900.
Galons, J. P., Altbach, M. I., Paine-Murrieta, G. D., Taylor, C. W. & Gillies, R. J. (1999) Early increases in breast tumor xenograft water mobility in response to paclitaxel therapy detected by non-invasive diffusion magnetic resonance imaging. Neoplasia, 1, 113-7.
Hagslatt, H., Jonsson, B., Nyden, M. & Soderman, O. (2003) Predictions of pulsed field gradient NMR echo-decays for molecules diffusing in various restrictive geometries. Simulations of diffusion propagators based on a finite element method. J Magn Reson, 161, 138-47.
Harkins, K. D., Galons, J. P., Secomb, T. W. & Trouard, T. P. (2009) Assessment of the effects of cellular tissue properties on ADC measurements by numerical simulation of water diffusion. Magn Reson Med, 62, 1414-22
Hwang, S. N., Chin, C. L., Wehrli, F. W. & Hackney, D. B. (2003) An image-based finite difference model for simulating restricted diffusion. Magn Reson Med, 50, 373-82.
Junzhong, X. & et al. (2007) Numerical study of water diffusion in biological tissues using an improved finite difference method. Physics in Medicine and Biology, 52, N111.
Kamel, I. R., Liapi, E., Reyes, D. K., Zahurak, M., Bluemke, D. A. & Geschwind, J. F. (2009) Unresectable hepatocellular carcinoma: serial early vascular and cellular changes after transarterial chemoembolization as detected with MR imaging. Radiology, 250, 466-73.
Lee, K. C., Moffat, B. A., Schott, A. F., Layman, R., Ellingworth, S., Juliar, R., Khan, A. P., Helvie, M., Meyer, C. R., Chenevert, T. L., Rehemtulla, A. & Ross, B. D. (2007) Prospective early response imaging biomarker for neoadjuvant breast cancer chemotherapy. Clin Cancer Res, 13, 443-50.
Moffat, B. A., Chenevert, T. L., Lawrence, T. S., Meyer, C. R., Johnson, T. D., Dong, Q., Tsien, C., Mukherji, S., Quint, D. J., Gebarski, S. S., Robertson, P. L., Junck, L. R., Rehemtulla, A. & Ross, B. D. (2005) Functional diffusion map: a noninvasive MRI biomarker for early stratification of clinical brain tumor response. Proc Natl Acad Sci U S A, 102, 5524-9.
Moseley, M. E., Cohen, Y., Mintorovitch, J., Chileuitt, L., Shimizu, H., Kucharczyk, J., Wendland, M. F. & Weinstein, P. R. (1990) Early detection of regional cerebral ischemia in cats: comparison of diffusion- and T2-weighted MRI and spectroscopy. Magn Reson Med, 14, 330-46.
Murday, J. S. & Cotts, R. M. (1968) Self-Diffusion Coefficient of Liquid Lithium, AIP.
Pickles, M. D., Gibbs, P., Lowry, M. & Turnbull, L. W. (2006) Diffusion changes precede size reduction in neoadjuvant treatment of breast cancer. Magn Reson Imaging, 24, 843-7.
Schachter, M., Does, M. D., Anderson, A. W. & Gore, J. C. (2000) Measurements of Restricted Diffusion Using an Oscillating Gradient Spin-Echo Sequence. Journal of Magnetic Resonance, 147, 232-237.
Schraml, C., Schwenzer, N. F., Clasen, S., Rempp, H. J., Martirosian, P., Claussen, C. D. & Pereira, P. L. (2009) Navigator respiratory-triggered diffusion-weighted imaging in the follow-up after hepatic radiofrequency ablation-initial results. J Magn Reson Imaging, 29, 1308-16.
Stejskal, E. O. & Tanner, J. E. (1965) Spin Diffusion Measurements: Spin Echoes in the Presence of a Time-Dependent Field Gradient. Journal of Chemical Physics, 42, 288-+.
Stepisnik, J. (1981) Analysis of NMR self-diffusion measurements by a density matrix calculation. Physica B+C, 104, 350-364.
Szafer, A., Zhong, J. & Gore, J. C. (1995) Theoretical model for water diffusion in tissues. Magn Reson Med, 33, 597-712.
Tanner, J. E. & Stejskal, E. O. (1968) Restricted Self-Diffusion of Protons in Colloidal Systems by the Pulsed-Gradient, Spin-Echo Method. The Journal of Chemical Physics, 49, 1768-1777.
Theilmann, R. J., Borders, R., Trouard, T. P., Xia, G., Outwater, E., Ranger-Moore, J., Gillies, R. J. & Stopeck, A. (2004) Changes in water mobility measured by diffusion MRI predict response of metastatic breast cancer to chemotherapy. Neoplasia, 6, 831-7.
Thoeny, H. C. & Ross, B. D. (2010) Predicting and monitoring cancer treatment response with diffusion-weighted MRI. J Magn Reson Imaging, 32, 2-16.
Warach, S., Chien, D., Li, W., Ronthal, M. & Edelman, R. R. (1992) Fast magnetic resonance diffusion-weighted imaging of acute human stroke. Neurology, 42, 1717-23.
Yu, J. S., Kim, J. H., Chung, J. J. & Kim, K. W. (2009) Added value of diffusion-weighted imaging in the MRI assessment of perilesional tumor recurrence after chemoembolization of hepatocellular carcinomas. J Magn Reson Imaging, 30, 153-60.
Freeman et al., "Phase and Intensity Anomalies in Fourier Transform NMR", Journal of Magnetic Resonance 4, 366-383 (1971).

(56) References Cited

OTHER PUBLICATIONS

Katz, Russell, "Biomarkers and Surrogate Markers: An FDA Perspective", NeuroRx: The Journal of the American Society for Experimental NeuroTherapeutics vol. 1, 189-195, (Apr. 2004).

Warntjes et al., "Novel Method for Rapid, Simultaneous T1, T*2, and Proton Density Quantification", Magnetic Resonance in Medicine 57:528-537 (2007).

Deoni et al., "Gleaning Multicomponent T1 and T2 Information From Steady-State Imaging Data", Magnetic Resonance in Medicine 60:1372-1387 (2008).

Pagani et al., "Intercenter Differences in Diffusion Tensor MRI Acquisition", Journal of Magnetic Resonance Imaging 31:1458-1468 (2010).

Zhu et al., "Quantification of accuracy and precision of multi-center DTI measurements: A diffusion phantom and human brain study", NeuroImage 56 (2011) 1398-1411.

Ma et al., "Magnetic resonance fingerprinting", Macmillan Publishers Limited vol. 495; 187-193 (2013).

Jovicich et al., "Multisite longitudinal reliability of tract-based spatial statistics in diffusion tensor imaging of healthy elderly subjects", NeuroImage 101 (2014) 390-403.

\* cited by examiner

Table 1)

| Step # | TR (ms) | Flip Angle (deg) |
|---|---|---|
| 1 | 420 | 45 |
| 2 | 10 | 10 |
| 3 | 10 | 40 |
| 4 | 10 | 15 |
| 5 | 10 | 35 |
| 6 | 10 | 20 |
| 7 | 10 | 25 |
| 8 | 10 | 30 |
| 9 | 10 | 90 |

METHOD OF GENERATING REPRODUCIBLE QUANTITATIVE MAGNETIC RESONANCE DATA

CROSS REFERENCE

This application claims priority to U.S. Provisional Patent Application No. 61/979,961 filed Apr. 15, 2014, and U.S. Provisional Patent Application No. 61/976,713 filed Apr. 8, 2014, the specification(s) of which is/are incorporated herein in their entirety by reference.

FIELD OF THE INVENTION

The present invention relates to the field of gathering quantitative magnetic resonance (QMRI) data for research purposes

BACKGROUND OF THE INVENTION

The use of surrogate imaging biomarkers as primary measures of disease state and progression has gained favor over the past decade. Nuclear magnetic resonance spectroscopy (NMRS) and magnetic resonance imaging (MRI) are formidable non-invasive tools for quantitatively interrogating materials. This can be attributed to the fact that MR measurements can be sensitized to a number of sample properties. A set of magnetic characteristics may well be unique to a one type of nucleus, chemical structure, chemical compound, material, or dynamic process in a sample. When present, the magnetic properties of a sample will be altered and MR experimental protocol may be designed such that measurements will be sensitive to the change.

The ability to ascertain how factors like those listed above alter the magnetic properties of a sample quantitatively could provide a wealth of information useful for determining the composition and condition of a sample. Where MRI methods are employed, these quantitative measures could be correlated with spatial locations within the sample to yield information about the internal organization of differentiated materials. In conjunction with its non-destructive nature, these properties make NMRS and MRI excellent choices for mining information about the static and dynamic properties of living biological systems. Developing the ability to extract quantitative information about living tissue using NMRS and MRI methods could help researchers and clinicians identify subtle changes in tissue properties with greater sensitivity and specificity. It follows that such methods may be used to identify and map surrogate biomarkers for use in research, diagnosis, and monitoring of disease progression as well as offer a safe means of evaluating drug efficacy.

The field of MRI concerned with generating quantitative maps of sample properties is known as quantitative MRI (QMRI). The use of QMRI in research and clinical practice constitutes a significant paradigm shift from the qualitative methods used to interpret property weighted images. Qualitative assessment methods are employed where images are sensitized or "weighted" to a particular property, e.g. $T_1$, $T_2$, or diffusion. Within the resulting image, relative intensity may differ from area to area. While weighting implies that contrast is thought to be primarily due to a certain property, it is accepted that other properties influence the intensities in the resulting image. By definition, attempts are not made to quantitatively determine contributions from other properties that are likely present. In QMRI, the objective is to correlate the quantified or measured value of a property of interest with a spatial location in a sample. This can be done in order to glean a better understanding of the chemical, structural, or dynamic properties of the sample. It could also identify improved imaging biomarkers thus enhancing the ability to extract information about the condition of a biological sample.

When using MRI to generate images for qualitative evaluation, the multiplicity of magnetic properties to which the image can be sensitized to is often considered one of the strengths of the modality. However, quantitatively separating the contributions to the measured MR signal, used for image reconstruction, from each influence is extremely challenging. Attempting to accurately measure or reproducibly quantify a property using MR methods is a complicated endeavor.

A number of MR studies have been conducted wherein with the careful quantification of an MR parameter in mind. Historically the methods used in such studies have required long scan times for data collection, making them unsuitable for clinical use. Recently, two promising QMRI methods have been reported. In multicomponent driven equilibrium single pulse observation of $T_1/T_2$ (mcDESPOT), imaging data is collected over the course of several steady state MR experiments. A multicompartment model of biological tissue is then implemented using a matrix formalism in order to analyze the results. This method has been employed to study neurodegenerative diseases as well as brain development. The scan times of roughly 30 minutes have been reported in these studies. It has been suggested that, given the complexity of the biological tissue model used for analysis and signal to noise in the steady state measurements, longer scan times would be required to improve quantitative confidence in the resulting parameters values. Additionally, it has been known for some time that measurements made using periodic and steady state sequences are not strictly periodic. More recently a method which employs an aperiodic sequence of excitation pulses and measurement sensitizing strategies has been described. Magnetic resonance fingerprinting (MRF) has been used to generate multiple parametric maps from data collected over the course of an imaging experiment that required only 12 seconds of scan time. The short scan times required for imaging may make the method extremely attractive to researchers and clinicians alike. However, because of the aperiodic nature of the MR sequence, measurements cannot be assumed to be equally weighted. Each measurement is comprised of a full, under sampled, imaging data set to be used for reconstruction. MRF is a relatively new method and the full implications of collecting data in this manner are not well understood.

The present invention develops a novel QMRI method which may produce repeatable MR data wherein the measurements may be assumed to be equally weighted. This allows for the rapid collection of a large amount of MR data which may be well suited for quantitative analysis. The present invention has surprising results of showing that, starting from a state of near zero bulk magnetization, as contrasted with starting from a presumed equilibrium configuration, may lead to more repeatable outcomes, allowing statistical strengthening of results by combining repeated measurements. And reaching states of near zero magnetization from arbitrary post-measurement states may be achieved very quickly by means of nulling sequences.

This result is surprising because the prior art has mostly striven to allow sufficient time for the specimen to relax toward the equilibrium configuration between repeated measurements, which considerably lengthens the processes of collecting an ensemble of measurements. And this has not been shown to provide consistently repeatable results of good statistical quality. Relaxation toward equilibrium configuration occurs asymptotically with exponential approach, whose time constant is largely determined by physical characteristics of the specimen. Relaxation times with e-folding periods ranging from 2000 ms to 4000 ms are commonplace where cerebrospinal fluid and water are primary constituents of the specimen. There has been considerable documented variation in how close to steady state equilibrium the starting conditions of repeated measurements may have been, which can only be overcome by waiting undesirably long times between measurements.

DETAILED DESCRIPTION OF PREFERRED EMBODIMENTS

Figure 1:
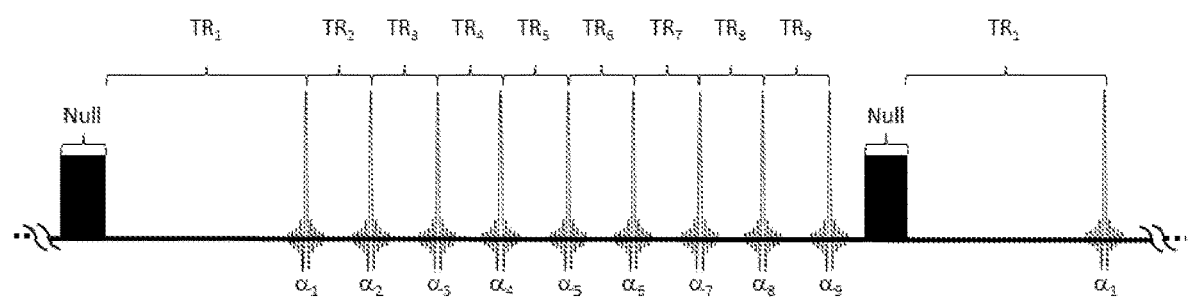
FIG. 1 shows a timeline of the method of the present invention

The present invention is a method for obtaining reproducible quantitative magnetic resonance data about a sample to be analyzed, which allows for the rapid collection of a large amount of data that is well suited for quantitative analysis. The method comprises performing a nulling sequence upon a sample to be analyzed, where the nulling sequence comprises of a series of applied changes to the magnetic field of the sample, which reduces all components of the magnetization in the sample to near zero magnitude. After performing the nulling sequence, one or more excitation steps are performed, where each excitation step comprises of applying an excitation pulse to the sample, followed by a period during which one or more alterations to the magnetic field may be applied via the NMR equipment and by one or more magnetic resonance data collection periods during which measurements are taken. The process of performing an excitation pulse, the manner in which the NMR equipment may be used to alter the magnetic field, and the collection of magnetic resonance data will be well known to one skilled in the art.

Because the magnetization of the sample is reduced to near zero prior to performing the sequence of excitation steps, the evolution of the magnetic field can be inferred to be deterministic and repeatable every time the same sequence of excitation steps is applied following a nulling sequence. This allows measurements to be equally weighted, which allows for improved signal to noise ratios through signal averaging.

Optionally, an alternative embodiment of the present invention may additionally comprise performing a nulling step, which comprises of a waiting period after the application of the nulling sequence, during which no excitation pulse or other electromagnetic field is applied to the sample. This allows the magnetization of the sample to regrow from a value of zero. Because the nulling sequence is applied prior to the nulling step, the regrowth can be assumed to follow a similar deterministic path for every application of the nulling sequence.

Optionally, the magnetic field of the sample may be manipulated excitation step over the course of any given step in order to sensitize the measurements to a variety of the sample's properties. Provided the sequence of manipulations is the same from one repetition of the sequence of excitation steps to the next, the measurements take will be reproducible from one repetition to the next.

In another embodiment, the method of the present invention may be performed repeatedly upon a sample using an identical sequence of excitation steps. Based on analysis below, the sequences of measurements obtained from each iteration of the method can be reasonably assumed to be identical to within a quantifiable tolerance. After obtaining the measurements for each iteration of the sequence, the measurement or measurements obtained from each excitation step can be averaged with those obtained at the same excitation step in every other iteration of the sequence, to obtain an improved signal to noise ratio for the measurement or measurements in each step.

In another embodiment, the method of the present invention may be performed repeatedly upon a sample using a sequence of excitation steps that is differentiated after a certain point. In this embodiment, there may be two or more versions of the sequence, where the first N excitation steps are identical. This allows the first N excitation steps to be used to take measurements of a property that is more difficult to measure, which requires a larger number of samples to average over. The subsequent measurements in each sequence can then be used to measure other properties and each sequence repeated an appropriate number of times to obtain a desired signal to noise ratio. For example, suppose we want to measure property A, B, and C. Property A has a lot signal to noise ratio and requires 100 samples to average over to improve the signal to noise ratio. Properties B and C have a higher signal to noise ratio and only require 50 samples to average over. Thus we can create sequences X and Y, where the first N excitation steps of both X and Y are identical, and which measure A. The subsequent N+1 to M excitation steps of X measure property B, while the N+1 to Mth excitation step of Y measure C. By performing sequence X 50 times and sequence Y 50 times, we end up with 100 samples that measure A, and 50 samples each for B and C. Note that the more difficult properties to measure must be included at the beginning of the sequences.

An excitation step may include one or more time varying magnetic fields. Time varying magnetic fields may be applied for a number of purposes including but not limited to:
1) Excitation for the purpose of data collection.
2) Slice selection
3) Rotation of the magnetization about any spatial axis for the purpose of magnetization refocussing
4) Rotation of the magnetization about any spatial axis for the purpose of sensitizing measurements sample properties.
5) Magnetization spoiling
6) Spin Species Suppression Time varying magnetic fields may differ from one another in any number of ways which include, but are not limited to:
1) Shape in the temporal and/or spectral domain
2) Strength: the amplitude of one or more of the components included in the spectral description.
3) Duration
4) Phase: of one or more components included in the spectral description.

An excitation step may include the application of one or more static or time dependent magnetic field gradients. A static or time dependent field gradient may be applied for a number of purposes including but not limited to:
1) Spatial encoding for the purpose of imaging.
2) Slice selection.
3) Spin Species Suppression
4) Magnetization refocussing.
5) Magnetization Spoiling
6) Motion encoding for the purpose of sensitizing measurements to any number of sample properties including but not limited to:
   a. Flow
   b. Diffusion
   c. Periodic Motion
7) Back projection (sample preparation and data acquisition)

Static or time varying gradients may differ from one another in any number of ways including but not limited to:
1) Direction of spatial dependence
2) Dependence on spatial direction
3) Time dependence of 1 and 2.

The present invention comprises of a novel QMRI method. The method is based on the application of a linear combination of excitation pulses and MR measurement sensitizing strategies following a nulling sequence to be described in detail below. Multiple differentiated measurements can be made over the course of each repetition of the sequence. This allows for the rapid collection of a large amount of imaging data which is well suited for quantitative analysis. Additionally, the application of a nulling sequence makes the assumption that measurements are equally weighted when made at corresponding points in the sequence extremely robust. The fact that measurements can be assumed to be equally weighted also means that measurements can be repeated, allowing for improvement of signal to noise (SNR) through signal averaging. In addition, simulated results will be shown that suggest that measurements made using the method would be sensitive to changes in tissue composition.

The following basic equations are derived in order to provide the reader with a pedagogical example. Similar derivations can be done in which other influences, e.g. diffusion and off resonance excitation pulses, are considered. Unless otherwise indicated, the laboratory frame of reference is used in the development of the mathematical framework for the method. In the coordinate system used for the equations and derivations that follow, the z axis is oriented parallel to the primary imaging field. The x and y axes lie in a plane perpendicular to the primary field. When a sample of water is immersed in a strong magnetic field a magnetic dipole moment per unit volume is induced. The vector quantity used to describe this moment is known as magnetization. Magnetization is manipulated to induce the signal observed in MR experiments. The phenomenological Bloch equations, developed by Felix Bloch in 1956, are central to our understanding of how the magnetization associated with a sample evolves over the course of an MR experiment.

$$\frac{dM_x(t)}{dt} = \gamma(M(t) \times B(t))_x - \frac{M_x(t)}{T_2} \qquad (1)$$

$$\frac{dM_y(t)}{dt} = \gamma(M(t) \times B(t))_y - \frac{M_y(t)}{T_2} \qquad (2)$$

$$\frac{dM_z(t)}{dt} = \gamma(M(t) \times B(t))_z - \frac{M_z(t) - M_{z0}(t)}{T_{12}} \qquad (3)$$

In the equations above, gamma ($\gamma$) is the gyromagnetic ratio of the nuclei of interest. The three components of a vector that describes the time dependent magnetization (M(t)) associated with a volume element, known as a voxel, located at a position r within a sample are $M_x(t)$, $M_y(t)$, and $M_z(t)$. The applied magnetic field B(t) may be a function of position and time. The characteristic times used to describe the influence of spin-lattice and spin-spin interactions, $T_1$ and $T_2$ respectively, will be considered constant with respects to time in this report. The thermal equilibrium value of the magnetization ($M_{z0}$) lays along the z axis, parallel to the primary imaging field. The Bloch equations and its variants can be used to predict the response of magnetization to the influence of time dependent changes in the applied magnetic field generated by the imaging equipment or describe its evolution following these perturbations. Where more than one species of nuclei is present and the differentiated pools are in exchange the Bloch-McConnell equations can be used to describe the evolution of the magnetization for each pool. For example, where two pools are present, pools A and B, six equations are required for this endeavor:

$$\frac{dM_{xA}(t)}{dt} = \gamma(M(t) \times B_A(t))_{xA} - K_{AB}M_{xA} + K_{BA}M_{xB} - \frac{M_{xA}(t)}{T_{2A}} \qquad (4)$$

$$\frac{dM_{xB}(t)}{dt} = \gamma(M(t) \times B_B(t))_{xB} - K_{BA}M_{xB} + K_{AB}M_{xA} - \frac{M_{xB}(t)}{T_{2B}} \qquad (5)$$

$$\frac{dM_{yA}(t)}{dt} = \gamma(M(t) \times B_A(t))_{yA} - K_{AB}M_{yA} + K_{BA}M_{yB} - \frac{M_{yA}(t)}{T_{2A}} \qquad (6)$$

$$\frac{dM_{yB}(t)}{dt} = \gamma(M(t) \times B_B(t))_{yB} - K_{BA}M_{yB} + K_{AB}M_{yA} - \frac{M_{yB}(t)}{T_{2B}} \qquad (7)$$

$$\frac{dM_{zA}(t)}{dt} = \gamma(M(t) \times B_A(t))_{zA} - K_{AB}M_{zA} + K_{BA}M_{zB} - \frac{M_{zA}(t) - M_{zA0}(t)}{T_{1A}} \qquad (8)$$

$$\frac{dM_{zB}(t)}{dt} = \gamma(M(t) \times B_B(t))_{zB} - K_{BA}M_{zB} + K_{AB}M_{zA} - \frac{M_{zB}(t) - M_{zB0}(t)}{T_{1B}} \qquad (9)$$

In the equations above, the three components of the magnetizations for each pool are present and differentiated from one another through the use of the subscripts A and B. Note that there are subscripts on the magnetic field vectors, $B_A(t)$ and $B_B(t)$. Nuclei immersed in the same imaging field at nearly the same location in a sample may experience different local magnetic fields. This may occur when nuclei are attached to different chemical compounds. The influence of neighboring nuclei may change the magnitude of the field for the nuclei of interest. For example, when imaging proton density, the hydrogen nuclei attached to water molecules and those attached to lipid chains in fat precess at observably different frequencies. The coefficients $K_{AB}$ and $K_{BA}$ mediate exchange between the two pools.

$$K_{AB} = \frac{1}{\tau_A} \qquad (10)$$

$$K_{BA} = \frac{1}{\tau_B} \qquad (11)$$

$K_{AB}$ can be interpreted as the reciprocal of the expectation value of the dwell time for a nuclei in pool A and $K_{BA}$ as the dwell time for a nuclei found in pool B. Under the assumption of exchange equilibrium they can be related to one another $$M_{z0A}K_{AB} = M_{z0B}K_{BA} \qquad (12)$$

It should be kept in mind that these equations can be solved for an infinite number of situations using any number of analytical or numerical methods. In the following section, the solutions for two example cases are presented for the sake of describing the sequence proposed. The following equations describe the evolution of the magnetization at a single voxel within the sample. The magnetic properties of each species are assumed to be uniform within the volume and the spatial dependence of the magnetization is omitted from the equations. The first case of interest is the application of a rotating magnetic field, referred to colloquially as an excitation pulse, because it typically rotates at a frequency the lies within the radio spectrum for clinical MRI systems. The second situation is a period of time, over which the MR system is not used to make any changes to the primary field. Where a convenient matrix formalism is employed, excitation pulses and relaxation periods (TRs) can be represented as matrix operators.

The multicomponent magnetization can be described using six component arrays.

$$M = \begin{bmatrix} M_{xA}(t) \\ M_{xB}(t) \\ M_{yA}(t) \\ M_{yB}(t) \\ M_{zA}(t) \\ M_{zB}(t) \end{bmatrix} \quad (13)$$

In these experiments, the signal is proportional to the transverse component of the magnetization $$M_T = \begin{bmatrix} M_x \\ M_y \end{bmatrix} = \begin{bmatrix} M_{xA} + M_{xB} \\ M_{yA} + M_{yB} \end{bmatrix}. \quad (14)$$

The orientation of the z-axis has been chosen such that it is parallel to the primary magnetic field. The excitation pulse discussed here is a rotating magnetic field. In the laboratory frame of reference, the x-axis will be the direction defined by the initial orientation of the magnetic field associated with the excitation pulse. It will be assumed that the excitation pulse rotates at the same frequency and in the same direction as a proton immersed in the primary imaging field. Additionally, it is assumed that the pulse is applied over an extremely short duration. Finally, it is assumed that the magnetic field associated with the excitation pulse is small compared to the primary imaging field. These assumptions are used in other similar derivations. The effect of an excitation pulse is to rotate the magnetization about the x-axis through a polar angle $\alpha$. The idealized matrix operator for an excitation pulse is given by $$R(\alpha_n) = \begin{bmatrix} 1 & 0 & 0 & 0 & 0 & 0 \\ 0 & 1 & 0 & 0 & 0 & 0 \\ 0 & 0 & \cos(\alpha_n) & 0 & \sin(\alpha_n) & 0 \\ 0 & 0 & 0 & \cos(\alpha_n) & 0 & \sin(\alpha_n) \\ 0 & 0 & -\sin(\alpha_n) & 0 & \cos(\alpha_n) & 0 \\ 0 & 0 & 0 & -\sin(\alpha_n) & 0 & \cos(\alpha_n) \end{bmatrix}. \quad (15)$$

As the method described in this invention prescribes the application of several excitation pulses with one repeated sequence, the subscripted "n" next to the angles in the above matrix is used indicate that the matrix is the operator for the nth pulse in the sequence. The effect of an applied excitation pulse can now be modeled $$M_n^+ = R(\alpha_n) M_n^- \quad (16)$$

where $M_n^-$ and $M_n^+$ are the magnetization found before and after the applied excitation pulse respectively.

Evolution of the magnetization over time periods when the primary field is left undisturbed is slightly more complicated. In order to relate the magnetization found before the TR period to that found after, two addition matrices $$A = \begin{bmatrix} -\frac{1}{T_{2A}} - K_{AB} & K_{BA} & \omega_A & 0 & 0 & 0 \\ K_{AB} & -\frac{1}{T_{2B}} - K_{BA} & 0 & \omega_B & 0 & 0 \\ -\omega_A & 0 & -\frac{1}{T_{2A}} - K_{AB} & K_{BA} & 0 & 0 \\ 0 & \omega_B & K_{AB} & -\frac{1}{T_{2B}} - K_{BA} & 0 & 0 \\ 0 & 0 & 0 & 0 & -\frac{1}{T_{1A}} - K_{AB} & K_{BA} \\ 0 & 0 & 0 & 0 & K_{AB} & -\frac{1}{T_{1B}} - K_{BA} \end{bmatrix} \quad (17)$$

and $$M'_{z0} = \begin{bmatrix} 0 \\ 0 \\ 0 \\ 0 \\ \dfrac{M_{z0A}}{T_{1A}} \\ \dfrac{M_{z0B}}{T_{1b}} \end{bmatrix} \quad (18)$$

are defined.

In equation 17, the off diagonal matrix elements $\omega_a$ and $\omega_b$ are the rates of precession for the protons in pool A and B respectively. With these two matrices defined, the evolution of the magnetization over the course of the TR time period can be described $$\frac{dM}{dt} = AM + M'_{z0}. \tag{19}$$

In the sequence being described here, the sequential application of an excitation pulse is followed by a TR period several times. This sequential application of these two will be referred to as an excitation step. It should be kept in mind that an excitation step may be comprised of more than just the two operations listed, but the two will suffice for the sake of describing the method. The state of the magnetization following an excitation pulse can now be related to the magnetization at points in time immediately following the previous excitation pulse, $$M_{n+1} = R(\alpha_{n+1})[\exp(ATR_{n+1})M_n + (\exp(ATR_{n+1})-I)A^{-1}M'_{z0}]. \tag{20}$$

In the example of the method of this invention, nine sequential excitation steps will be included in a repeated periodic sequence.

The nulling sequence is critical to the method described here. A nulling sequence is any series of applied changes to the primary magnetic field intended to reduce all components of the magnetization to negligible magnitudes. In one embodiment of nulling sequences, the use of a rapid succession of RF saturation pulses designed to produce maximal phase dispersion, and with each pulse followed immediately by strong magnetic spoiler gradients designed to eliminate the transverse component of the magnetization, colloquially referred to as "crushers", might work well. Such nulling sequences might require a fraction of the time normally required to await unaided asymptotic relaxation of the specimen sufficiently toward the steady state equilibrium configuration.

However, the distinction between the null state and the equilibrium state is important to keep in mind: In the equilibrium state a thermal population, described by the Boltzmann distribution, has the protons of the specimen existing as a mixture of two nearly equal energy states, with a slight preference for, and higher population among, the lower energy state. These energy states correspond to parallel and anti-parallel proton spin alignments along the direction of the primary static magnetic reference field. The magnetizations induced by these two states have opposing sense. And with a slight equilibrium population difference between the two states the result may be a measurable net bulk magnetization of the specimen along the direction associated with the lower energy state spin alignment. By contrast, after application of a nulling sequence, we may seek to achieve a net near-zero bulk magnetization. We may achieve that null state by rapidly decorrelating the spin states in the specimen.

Following the application of a nulling sequence, it is assumed that the response of the magnetization to the sequential application of excitation steps that follow will be the same if the excitation steps are the same. Where an identical sequence of excitation steps is used, measurements can faithfully be assumed to be equally weighted at corresponding time points in repetitions of the sequence. Though this assumption is made in the development of periodic and steady state sequences that do not include a nulling sequence, it has been shown that it is not strictly true for all circumstances.

It is important to note that repetitions of a sequence need not be conducted back to back. Rather different sequences of excitation steps may be used between nulling sequences and repetitions of any sequence may be conducted at periodic or aperiodic intervals. Additionally, consider two sequences which start with a nulling sequence, sequence 1 and sequence 2. Sequence 1 and sequence 2 comprise of N excitation steps and M excitation steps respectively. Where S is less than or equal to N and/or S less than or equal to M, if the first S excitation steps in sequence 1 are identical to the first S excitation steps in sequence 2, then measurements made at corresponding time points within those initial S excitation steps will be equally weighted.

The vector describing the state of the magnetization following a nulling sequence for a two component tissue model is simply $$M_{null} = \begin{bmatrix} 0 \\ 0 \\ 0 \\ 0 \\ 0 \\ 0 \end{bmatrix}. \tag{21}$$

By recursively applying equation 20, the state of the magnetization can be predicted at time points following each application of an excitation pulse in an N excitation step sequence comprising excitation pulses and TR periods. FIG. 1 shows an example of a simple nine excitation step sequence.

In FIG. 1, the nulling sequence is labeled "Null". Following the application of the nulling sequence, the time period $TR_1$ is significantly longer than the eight that follow. The initial TR need not be longer than the others, but here it allows for magnetization regrowth from a value of zero to the equilibrium value. $TR_1$ is followed by the excitation pulse $\alpha_1$ to complete the first excitation step. Excitation steps 2 through 9 are comprised of a shorter TR followed by an excitation pulse. Equation 20, with initial state from Equation 21, can be used to determine the state of the magnetization following the application of any excitation pulse by recursion of the equation from some earlier epoch to the excitation step number, n.

EXAMPLE 1

Figures 4, 5:
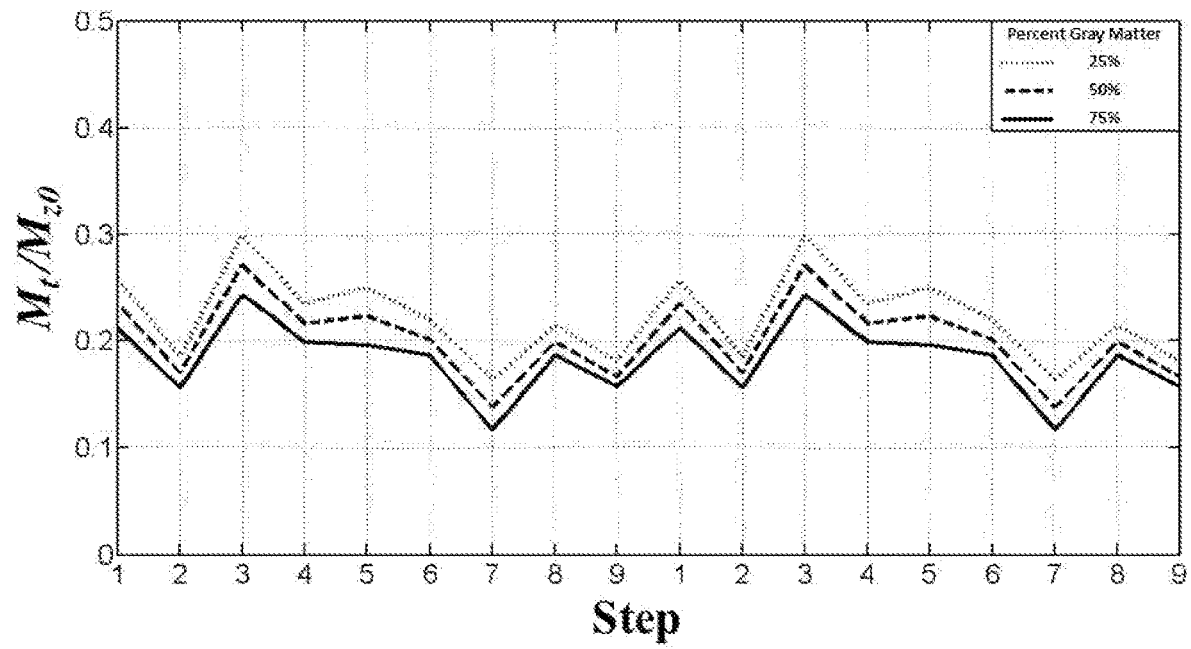
FIG. 4 shows an example set of results using the method of present invention using samples with differing percentages of grey vs. white matter
FIG. 5 shows an example sequence of excitation steps applied using the method of the present invention

In an example application of the method of the present invention, the nine excitation step sequence shown in FIG. 1 is used with a two compartment model of biological tissue. The TRs and flip angles selected for the nine excitation step sequence are shown in Table 1 (FIG. 5).

Each repetition of the sequence requires 500 ms. The model tissue is composed of 50% gray matter and 50% white matter. Pool A in the equations above is assigned biological parameter values similar to those reported for gray matter immersed in a 3T imaging field. A $T_1$ of 1350 ms and $T_2$ of 105 ms are used to describe pool A. Pool B is assigned relaxation values roughly equal to those reported for white matter in a 3T imaging field. A $T_1$ of 830 ms and a $T_2$ of 80 ms are used. In addition, it is assumed that the two pools differ in rotational frequency by 2 Hz. The two compartments are in exchange, $K_{AB}$ is set to 0.01 ms$^{-1}$. The state of the magnetization is determined at times following each applied excitation pulse over two repetitions of the sequence. The vector sum of the magnetization associated with the pools is then determined. The components are normalized to the sum of the equilibrium values of the two pools.

Figure 2:
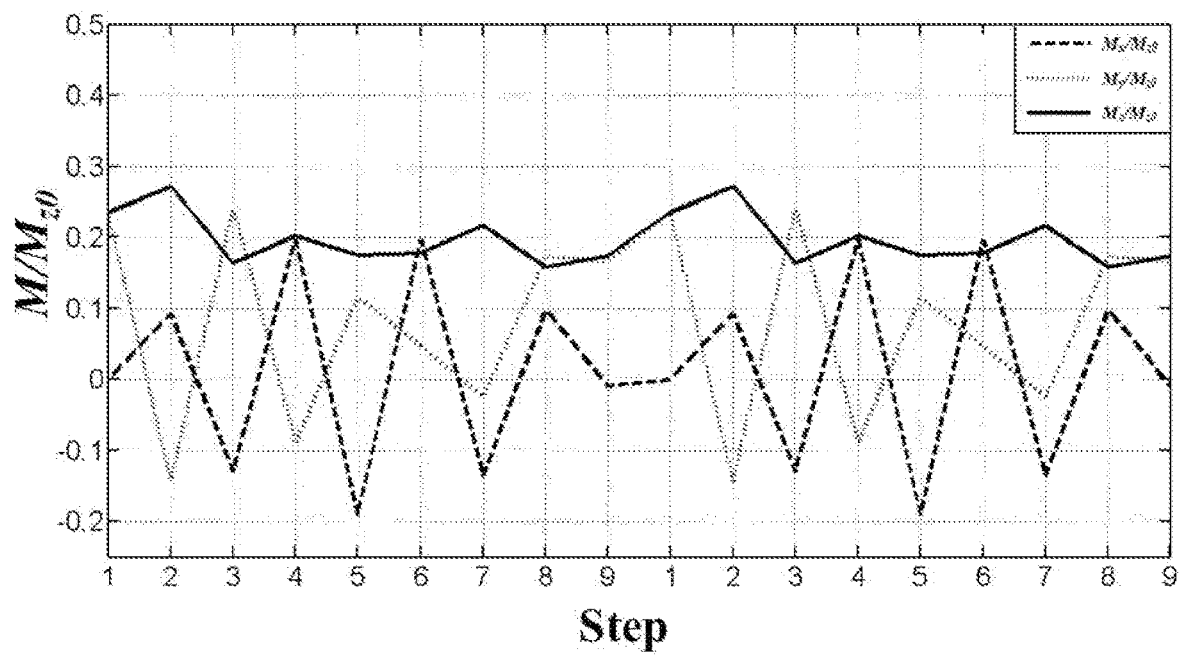
FIG. 2 shows an example set of results using the method of present invention

FIG. 2 shows example results for this simulation for the three normalized components. The solid black line connects values determined for $M_z/M_{z0}$, dashed lines for $M_x/M_{z0}$, and dotted lines for $M_y/M_{z0}$. All three components are equal at corresponding points in the repeated sequence. The MR signal intensity originating from the volume element described is proportional to the magnitude of the transverse component of the magnetization.

Figure 3:
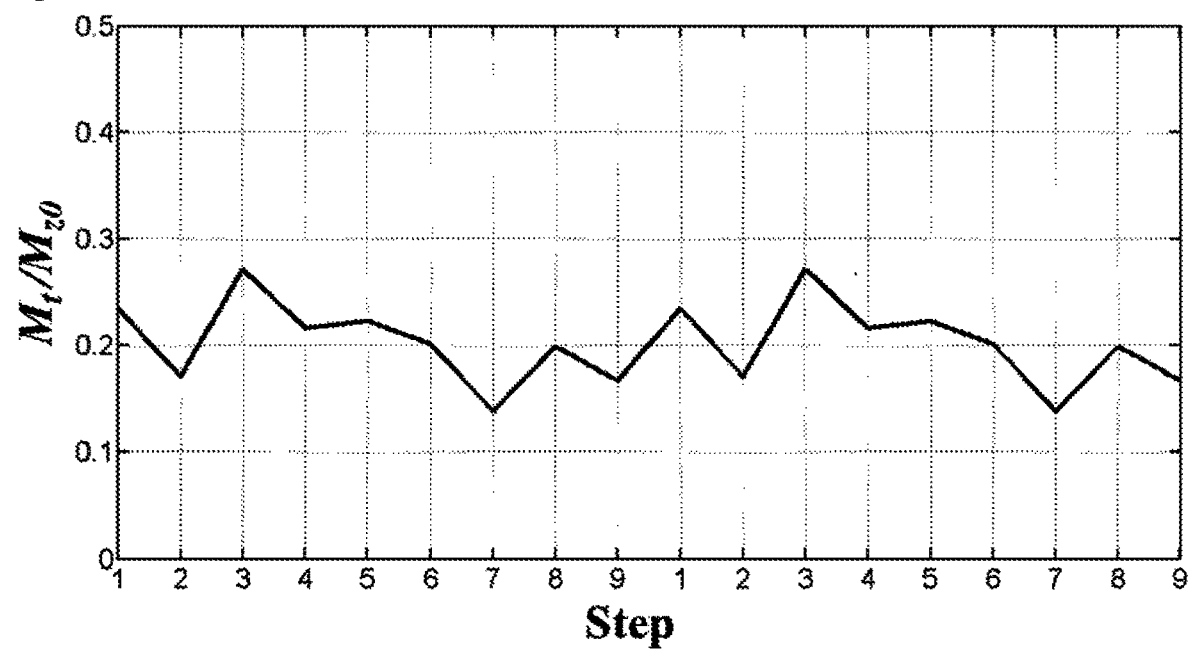
FIG. 3 shows an example set of results using the method of present invention

FIG. 3 shows the evolution of the magnitude of the element over the two repetitions of the sequence. Again, these values are repeated. In all cases, the simulated values agree with the values determined through the use of equations 20. These two figures serve to illustrate the fact that both the magnitude and the phase of the magnetization associate with each voxel contained within the sample will be repeated.

EXAMPLE 2

In this example, three final sets of simulations are conducted, using the same nine excitation step sequence, for voxels comprising different fractions of gray and white matter. In each case, $K_{AB}$ is set to 0.01 ms$^{-1}$, and $K_{BA}$ is calculated using equation 12. FIG. 4 shows the evolution of the magnitude of the transverse component of the magnetization for these three different voxels. The solid black shows the results of simulations conducted using a tissue model composed of 75% gray matter and 25% white matter, dashed lines represent results for 50% gray matter and 50% white matter, and the dotted line shows the results for 25% gray matter and 75% white matter.

Several properties make the method described herein well suited for extracting quantitative information from MRI data: Measurements are reproducible, the assumptions made in the development of the supporting quantitative theory are well satisfied, and the investigator should be able to collect large amounts of imaging data with great speed. Simulated experiments have also suggested that measurements made using this method can be sensitive to differences in tissue composition.

When attempting to generate parametric maps using MR methods, the ability to repeat a measurement under the assumption that the state of the magnetization is the same at different points in time may enable the experimentalist to increase the signal to noise of a measurement through signal averaging. If, for example, the objective of an experiment was to image nuclei that were low in abundance or characterized by extremely short relaxation times, this feature might be highly desirable or necessary. Simulated data used to generate FIGS. 2, 3 and 4 suggest that the transverse components of the magnetization, used to induce MR signal, are repeated. Where aperiodic sequences are employed, no two data sets are collected assuming equal weighting and SNR cannot be increased through signal averaging.

Where periodic and steady state sequences are employed to generate parametric maps, it is assumed that measurements are periodic and that the periodicity of the measurements is the same as that of the sequence used. While this assumption is employed to develop the mathematical framework used for the analysis of steady state data, it has been shown that it is not strictly true. The phase and magnitude of the measurements assumed to be equal may differ in phase and magnitude. Where a theoretical assumption is made but not necessarily valid, incorrect values can be calculated for modeled parameters. The introduction of a nulling sequence forces the magnetization into an identical state every time it is applied. Following a nulling sequence, the magnetization can be assumed to be identically prepared so long as the magnetic field is manipulated in the same manner. Again, FIGS. 2, 3 and 4 support this assertion.

The example of the method presented here, uses only nine excitation steps and the time period following the nulling sequence, $TR_1$, is significantly longer than $TR_2$ through $TR_9$. $TR_1$ is, in the example, is longer than all of the other TR periods combine. $TR_1$ is essentially a repeated sample preparation period required for regrowth of the magnetization along the z axis following a nulling sequence. The nine excitation step sequence used as an example would not be an efficient data collection strategy. However, a much larger number of excitation steps can be incorporated into a sequence. As increasingly complex tissue models with larger numbers of biological parameters are being employed for data analysis, it is likely that a large number of imaging data sets will be required to faithfully determine parameter values. The fact that the aperiodic method, MRF, calls for imaging data to be collected over hundreds or even thousands of excitation steps reflects this trend. A similar number of excitation steps could be used in the sequences described here. As excitation steps are added, the fraction of the sequence occupied by $TR_1$ would decrease, thereby increasing the efficiency of the method.

The method is sensitive to changes in biological tissue parameters. FIG. 4 shows the results of three separate simulations conducted using tissue models composed of gray and white matter. Solid black, dashed, and dotted lines are used to show the evolution of 75%/25% gray/white matter, 50%/50% gray/white matter, and 25%/75% gray/white matter respectively. Significant differences can be observed in the evolution of the magnetization in each simulated data set. This is a promising result, as no attempt has been made to optimize the method to detect changes in cerebral tissue composition.

In this report, a novel QMRI method is described. The results of simulated experiments are shown to support claims made regarding the performance of the method. In theory, the method possesses several desirable characteristic. First, a large number of differentiated measurements can be collected over a relatively short period of time. Secondly, measurements can be assumed to be equally weighted following a nulling excitation step so long as the series of excitation steps leading up to the measurements are identical. Thus measurements can be repeated and signal averaging can be used to improve SNR. Thirdly, the assumption that measurements made at corresponding points in time following the application of a nulling sequence is robust. Measurements will not suffer from the fluctuations in phase and intensity observed in steady state and periodic sequences. Finally, the results of simulated experiments, shown in this report, have indicated that measurements made through the use of this method would be sensitive to changes in biological tissue composition.

In some embodiments, the present invention may be effective to provide sufficient consistency of measurements such that room temperature quantum qubit computers could be constructed. Present day quantum computing is being attempted at cryogenic temperatures for its ability to control thermal noise contributions.

In other embodiments, the present invention may provide the degree of quantitative accuracy needed to pave the way toward non-invasive imaging chemical assays and labeled histological surveys of living tissue specimens. Presently, the use of NMR for non-invasive imaging lacks sufficient quantitative accuracy to provide this sort of detail, and provides mostly qualitative images subject to interpretation by trained examiners.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of estimating a property of a sample using quantitative magnetic resonance data, said method comprising:
   a. performing a nulling sequence, wherein the nulling sequence comprises a series of applied changes to the magnetic field of the sample, which reduces all components of the magnetization in the sample to near zero or zero magnitude, within measurable limits;
   b. performing a sequence of excitation steps, each excitation step comprising:
      i. applying a magnetic excitation pulse to the sample;
      ii. manipulating the magnetic field of the sample in order to sensitize the measurements to at least one sample property;
      iii. waiting a relaxation time;
      iv. obtaining a measurement of the magnetic field of the sample, wherein the measurement is a measure of the at least one sample property of that step; and
   c. repeating steps (a) and (b) to collect a plurality of measurements for each step in the sequence of excitation steps;
   d. averaging the plurality of measurements for each step of the sequence of excitations to obtain an estimate of the at least one sample property of each step in the sequence of excitation steps; and
   e. applying a time-dependent magnetic field to the sample in order to perform magnetization spoiling.

2. A method of estimating a property of a sample using quantitative magnetic resonance data, said method comprising:
   a. performing a nulling sequence, wherein the nulling sequence comprises a series of applied changes to the magnetic field of the sample, which reduces all components of the magnetization in the sample to near zero or zero magnitude, within measurable limits;
   b. performing a sequence of excitation steps, each excitation step comprising:
      i. applying a magnetic excitation pulse to the sample;
      ii. manipulating the magnetic field of the sample in order to sensitize the measurements to at least one sample property;
      iii. waiting a relaxation time;
      iv. obtaining a measurement of the magnetic field of the sample, wherein the measurement is a measure of the at least one sample property of that step; and
   c. repeating steps (a) and (b) to collect a plurality of measurements for each step in the sequence of excitation steps;
   d. averaging the plurality of measurements for each step of the sequence of excitations to obtain an estimate of the at least one sample property of each step in the sequence of excitation steps; and
   e. applying a time-dependent magnetic field to the sample in order to perform spin species suppression.

3. A method of estimating a property of a sample using quantitative magnetic resonance data, said method comprising:
   a. performing a nulling sequence, wherein the nulling sequence comprises a series of applied changes to the magnetic field of the sample, which reduces all components of the magnetization in the sample to near zero or zero magnitude, within measurable limits;
   b. performing a sequence of excitation steps, each excitation step comprising:
      i. applying a magnetic excitation pulse to the sample;
      ii. manipulating the magnetic field of the sample in order to sensitize the measurements to at least one sample property;
      iii. waiting a relaxation time;
      iv. obtaining a measurement of the magnetic field of the sample, wherein the measurement is a measure of the at least one sample property of that step; and
   c. repeating steps (a) and (b) to collect a plurality of measurements for each step in the sequence of excitation steps;
   d. averaging the plurality of measurements for each step of the sequence of excitations to obtain an estimate of the at least one sample property of each step in the sequence of excitation steps; and
   e. applying a time-dependent magnetic field to the sample in order to perform spin species suppression, magnetization spoiling, or back projection.

* * * * *